(12) United States Patent
Masinaei et al.

(10) Patent No.: US 9,408,875 B2
(45) Date of Patent: *Aug. 9, 2016

(54) COMPOSITIONS FOR REPAIR OF DEFECTS IN TISSUES, AND METHODS OF MAKING THE SAME

(71) Applicant: LifeNet Health, Virginia Beach, VA (US)

(72) Inventors: Leila Masinaei, Dubai (AE); Lloyd Wolfinbarger, Jr., Norfolk, VA (US); Silvia S. Chen, Virginia Beach, VA (US); Alyce Linthurst Jones, Virginia Beach, VA (US); Jingsong Chen, Virginia Beach, VA (US)

(73) Assignee: LifeNet Health, Virginia Beach, VA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/658,368

(22) Filed: Mar. 16, 2015

(65) Prior Publication Data

US 2015/0182559 A1 Jul. 2, 2015

Related U.S. Application Data

(63) Continuation of application No. 12/732,974, filed on Mar. 26, 2010, now Pat. No. 9,005,646, which is a continuation-in-part of application No. 12/188,127, filed on Aug. 7, 2008, now Pat. No. 9,132,208, and a continuation-in-part of application No. 12/394,629, filed on Feb. 27, 2009, now Pat. No. 8,309,106, which is a continuation of application No. 11/247,230, filed on Oct. 12, 2005, now Pat. No. 7,498,041.

(51) Int. Cl.

| | |
|---|---|
| *A61K 9/00* | (2006.01) |
| *A61L 27/36* | (2006.01) |
| *A61K 35/35* | (2015.01) |
| *A61L 27/56* | (2006.01) |
| *A61K 35/32* | (2015.01) |
| *A61K 47/22* | (2006.01) |
| *A61L 27/28* | (2006.01) |
| *A61F 2/28* | (2006.01) |
| *A61F 2/30* | (2006.01) |

(52) U.S. Cl.

CPC .............. *A61K 35/35* (2013.01); *A61K 35/32* (2013.01); *A61K 47/22* (2013.01); *A61L 27/28* (2013.01); *A61L 27/3604* (2013.01); *A61L 27/3608* (2013.01); *A61L 27/56* (2013.01); *A61F 2/28* (2013.01); *A61F 2/30756* (2013.01); *A61F 2310/00359* (2013.01); *A61L 2300/30* (2013.01); *A61L 2300/606* (2013.01); *A61L 2430/02* (2013.01)

(58) Field of Classification Search

CPC ....... A61K 35/00; A61K 35/32; A61K 35/36; A61K 9/00; A61L 27/3603; A61L 27/3604

See application file for complete search history.

(56) References Cited

U.S. PATENT DOCUMENTS

| | | |
|---|---|---|
| 4,522,753 A | 6/1985 | Yannas |
| 4,808,570 A | 2/1989 | Michaeli |
| 5,053,049 A | 10/1991 | Campbell |
| 5,350,583 A | 9/1994 | Yoshizato et al. |
| 5,531,791 A | 7/1996 | Wolfinbarger, Jr. |
| 5,556,430 A | 9/1996 | Gendler |
| 5,674,292 A | 10/1997 | Tucker et al. |
| 5,718,916 A | 2/1998 | Scherr |
| 5,776,193 A | 7/1998 | Kwan et al. |
| 5,888,987 A | 3/1999 | Haynes et al. |
| 5,948,428 A | 9/1999 | Lee et al. |
| 6,013,856 A | 1/2000 | Tucker et al. |
| 6,028,242 A | 2/2000 | Tucker et al. |
| 6,080,194 A | 6/2000 | Pachence et al. |
| 6,180,606 B1 | 1/2001 | Chen et al. |
| 6,187,047 B1 | 2/2001 | Kwan et al. |
| 6,306,169 B1 | 10/2001 | Lee et al. |
| 6,309,659 B1 | 10/2001 | Clokie |
| 6,309,670 B1 | 10/2001 | Heidaran et al. |
| 6,311,690 B1 | 11/2001 | Jefferies |
| 6,326,018 B1 | 12/2001 | Gertzman et al. |
| 6,334,968 B1 | 1/2002 | Shapiro et al. |
| 6,372,257 B1 | 4/2002 | Marchosky |

(Continued)

FOREIGN PATENT DOCUMENTS

| | | |
|---|---|---|
| WO | 99/19005 A1 | 4/1999 |
| WO | 2004/017915 A2 | 3/2004 |

(Continued)

OTHER PUBLICATIONS

Lee et al., "Sustained Release of Vascular Endothelial Growth Factor From Calcium-Induced Alginate Hydrogels Reinforced by Heparin and Chitosan," Transplantation Proceedings, 36: 2464-2465 (2004).
van Susante et al., "Culture of chondrocytes in alginate and collagen carrier gels," Acta Orthop Scand, 66: 549-556 (1995).
Marijinissen et al., "Tissue-engineered cartilage using serially passaged articular chondrocytes. Chondrocytes in alginate, combined in vivo with a synthetic (E210) or biologic biodegradable carrier (DBM)," Biomaterials, 21: 571-580 (2000).
Pound et al., "An ex vivo model for chondrogenesis and osteogenesis," Biomaterials, 28: 2839-2849 (2007).
Cho et al., "Fabrication and characterization of porous alginate/polyvinyl alcohol hybrid scaffolds for 3D cell culture," Journal of Biomaterials Science, Polymer Edition, 16: 933-947 (2005).
Shapiro et al., "Novel alginate sponges for cell culture and transplantation," Biomaterials, 18: 583-590 (1997).
Glicklis et al., "Hepatocyte Behavior Within Three-Dimensional Porous Alginate Scaffolds," Biotechnology & Bioengineering, 67: 344-353 (2000).

(Continued)

*Primary Examiner* — Ruth Davis
(74) *Attorney, Agent, or Firm* — RatnerPrestia

(57) ABSTRACT

Tissue repair compositions, particularly bone repair compositions, containing (a) bone fragments and (b) homogenized connective tissue, and methods for making the same are provided. Some of the inventive tissue repair compositions contain a radioprotectant. The compositions can be used in the form of an injectable gel, an injectable paste, a paste, a putty, or a rehydratable freeze-dried form. Kits for using such tissue repair compositions are also provided.

16 Claims, No Drawings

(56) References Cited

U.S. PATENT DOCUMENTS

| | | |
|---|---|---|
| 6,447,701 B1 | 9/2002 | Heschel et al. |
| 6,458,375 B1 | 10/2002 | Gertzman et al. |
| 6,461,630 B1 | 10/2002 | Tucker et al. |
| 6,504,079 B2 | 1/2003 | Tucker et al. |
| 6,576,249 B1 | 6/2003 | Gendler et al. |
| 6,679,918 B1 | 1/2004 | Benedict et al. |
| 6,793,675 B2 | 9/2004 | Shapiro et al. |
| 6,808,585 B2 | 10/2004 | Boyce et al. |
| 6,852,330 B2 | 2/2005 | Bowman et al. |
| 6,884,428 B2 | 4/2005 | Binette et al. |
| 6,933,326 B1 | 8/2005 | Griffey et al. |
| 7,001,551 B2 | 2/2006 | Meredith |
| 7,045,141 B2 | 5/2006 | Merboth et al. |
| 7,128,929 B1 | 10/2006 | Scherr |
| 7,131,994 B2 | 11/2006 | Mills et al. |
| 7,132,110 B2 | 11/2006 | Kay et al. |
| 7,498,040 B2 | 3/2009 | Masinaei et al. |
| 7,498,041 B2 | 3/2009 | Masinaei et al. |
| 7,824,701 B2 | 11/2010 | Binette et al. |
| 8,309,106 B2 | 11/2012 | Masinaei et al. |
| 9,132,208 B2 * | 9/2015 | Chen .................. A61L 27/3604 |
| 2002/0082694 A1 | 6/2002 | McKay |
| 2003/0003157 A1 | 1/2003 | Ohan et al. |
| 2004/0059364 A1 | 3/2004 | Gaskins et al. |
| 2004/0097612 A1 | 5/2004 | Rosenberg et al. |
| 2004/0230309 A1 | 11/2004 | DiMauro et al. |
| 2006/0067967 A1 | 3/2006 | Bowman et al. |
| 2006/0159663 A1 | 7/2006 | Lu et al. |
| 2006/0204544 A1 | 9/2006 | Sunwoo et al. |
| 2007/0065943 A1 | 3/2007 | Smith et al. |
| 2007/0083270 A1 | 4/2007 | Masinaei et al. |
| 2007/0093912 A1 | 4/2007 | Borden |
| 2007/0254041 A1 | 11/2007 | Drapeau et al. |
| 2008/0147197 A1 | 6/2008 | McKay |
| 2009/0024229 A1 | 1/2009 | Chen et al. |

FOREIGN PATENT DOCUMENTS

| | | |
|---|---|---|
| WO | 2004/045372 A2 | 6/2004 |
| WO | 2006/027622 A2 | 3/2006 |
| WO | 2006/076712 A2 | 7/2006 |

OTHER PUBLICATIONS

Avella et al., "Addition of glycerol plasticizer to seaweeds derived alginates: Influence of microstructure on chemical-physical properties," Carbohydrate Polymers, 69: 503-511 (2007).

Pongjanyakul et al., "Alginate-magnesium aluminum silicate films: Effect of plasticizers on film properties, drug permeation and drug release from coated tablets," International Journal of Pharmaceutics, 333: 34-44 (2007).

Ohta et al., "Novel heparin/alginate gel combined with basic fibroblast growth factor promotes nerve regeneration in rat sciatic nerve," Journal of Biomedical Materials Research Part A, 71: 661-668 (2004).

Lee et al., "Integration of layered chondrocyte-seeded alginate hydrogel scaffolds," Biomaterials, 28: 2987-2993 (2007).

Liao et al., "Controlled release from fibers of polyelectrolyte complexes," Journal of Controlled Release, 104: 347-358 (2005).

Extended European Search Report issued in related European Patent Application No. 09805294.7 dated Dec. 11, 2013.

* cited by examiner

COMPOSITIONS FOR REPAIR OF DEFECTS IN TISSUES, AND METHODS OF MAKING THE SAME

FIELD OF INVENTION

The present invention provides tissue repair compositions comprising homogenized connective tissue and bone fragments. The tissue repair compositions may be used to repair and regenerate tissues.

BACKGROUND OF THE INVENTION

The ability to promote tissue regrowth in vivo can facilitate wound healing and post-surgical recovery of patients who have suffered tissue damage or destruction. A variety of methods and compositions have been used to repair or regenerate bone tissue in vivo. The need for such methods and compositions is readily apparent, when considering that in 1999, approximately 500,000 bone graft procedures were performed in the United States alone. Ideal bone graft materials for use in such procedures possess characteristics necessary to induce new bone growth, namely osteoconductivity and osteoinductivity.

Osteoconductivity refers to a graft's ability to support the attachment of new osteoblasts and osteoprogenitor cells. The osteoconductive components of a graft provide an interconnected structure through which new cells can migrate and new blood vessels can form. Osteoinductivity refers to the ability of a graft to induce nondifferentiated stem cells or osteoprogenitor cells to differentiate into osteoblasts.

In 1998, nine out of ten bone graft procedures performed in the United States involved the use of either autograft or allograft bone tissue. Despite the benefits of autografts and allografts, the limitations of each have necessitated the pursuit of alternative graft materials. Using basic criteria necessary to a successful graft (e.g., osteoconduction and osteoinduction), investigators have developed several bone graft substitutes. These can contain a variety of materials, including natural and synthetic polymers, ceramics, and composites; and in some instances, production of bone graft substitutes can involve biotechnological strategies (i.e., factor- and/or cell-based strategies). Non-demineralized bone, such as freeze-dried cortical particulate, is the most often used osteoconductive bone grafting material.

Osteoinductive substances found in some bone graft substitutes are demineralized bone particles and/or powder. Contained in the extracellular matrix of bone tissue is a full cocktail of bone growth factors, proteins, and other bioactive materials necessary for osteoinduction and, ultimately, successful bone healing. To capitalize on this cocktail of proteins, bone tissue can be demineralized, leaving the osteoinductive agents in the demineralized bone matrix (DBM). Such osteoinductive DBM can be incorporated into a number of different bone graft substitutes.

While a number of different materials thought to enhance osteoconductivity (i.e., purified or partially purified polymers) have been used in bone graft substitutes, new, more easily prepared, osteoconductive/structural materials for combining with demineralized or non-demineralized bone to produce a bone graft substitute are desirable.

SUMMARY OF THE INVENTION

The present invention provides a carrier consisting of or consisting essentially of one or more homogenized connective tissues. An example of a connective tissue that may be homogenized to make the carrier of the present invention includes but are not limited to fascia.

Accordingly, the present invention also provides carrier compositions comprising a carrier consisting of or consisting essentially of one or more homogenized connective tissues and optionally, a carrier compound selected from the group consisting of antioxidants, water miscible polar organic compounds, water, natural polymers, synthetic polymers, antibiotics, antiviral agents, polysaccharides, extracellular matrix and a combination thereof.

The antioxidant in the carrier composition may be a radioprotectant, such as amino guanidine.

The water miscible polar organic compound may be glycerol.

Biologically active agents used for repairing and/or regenerating tissues may be added to the carrier composition. Examples of these agents include but are not limited to bone fragments, blood, blood products, bioactive factors, and/or cells.

The bone fragments may include a plurality of naturally occurring bone fragments, a plurality of synthetic bone fragments, or a combination thereof. The bone fragments may be demineralized bone fragments, non-demineralized bone fragments, or a combination thereof. Examples of demineralized bone fragments include demineralized bone particles and/or fibers. Examples of non-demineralized bone fragments include non-demineralized cancellous or cortical bone particles and/or fibers.

The addition of the biologically active agents to the carrier composition of the present invention produces a tissue repair composition. In one embodiment, the tissue repair composition of the present invention may include a carrier consisting of or consisting essentially of one or more homogenized connective tissues, one or more antioxidants, one or more water miscible polar organic compounds, one or more bone fragments, and one or more bioactive factors. In another embodiment, the carrier in the tissue repair composition of the present invention may consist of or consist essentially of homogenized fascia; the antioxidant in the tissue repair composition may be aminoguanidine; the water miscible polar organic compound may be glycerol; and the bone fragments may be demineralized bone fragments, non-demineralized bone fragments, synthetic bone fragments, or a combination thereof. The tissue repair composition of the present invention also may serve as a carrier composition for delivering biologically active agents such as bioactive factors or cells to the target site. The target site may be a site of injury or an implant site.

The carrier composition and the tissue repair composition of the present invention may be a freeze dried composition.

The present invention provides a method of making a carrier composition and/or tissue repair composition including (a) preparing a connective tissue homogenate consisting of or consisting essentially of one or more homogenized connective tissues; (b) preparing a carrier composition comprising mixing the connective tissue homogenate with a carrier compound to produce a carrier composition; and (c) optionally, mixing the carrier composition with bone fragments and/or biologically active agents to produce a composition for repairing tissue defects or for healing wounds. The method of the present invention may further comprise freeze-drying the carrier composition prior to step (c) or after step (c), but prior to implantation.

The bone fragments used for making the compositions of the present invention may be natural demineralized bone fragments, natural non-demineralized bone fragments, synthetic bone fragments, or a combination thereof.

The carrier compound used for making the compositions of the present invention may comprise a compound selected from the group consisting of antioxidants, water miscible polar organic compounds, water, natural polymers, synthetic polymers, antibiotics, antiviral agents, polysaccharides, and a combination thereof. The antioxidant may be a radioprotectant, such as aminoguanidine, and the water miscible polar organic compound may be a water replacement agent, such as glycerol. The method may further comprise mixing the tissue repair composition with a bioactive factor.

The present invention provides a method of promoting tissue repair or regeneration comprising applying a tissue repair composition of the present invention to a damaged tissue to promote repair or regeneration of the tissue. The tissue may be an osseous tissue, a cartilage, or a soft tissue. The present invention also include methods of using the tissue repair composition to heal or repair wounds or tissue defects.

The present invention provides a method of inducing bone or cartilage formation comprising applying the tissue repair composition of the present invention to an implant site to induce bone or cartilage formation.

The compositions of the present invention, in particular the tissue repair compositions, may be used for repairing or regenerating various tissues, such as osseous defect repair, wound repair, cartilage repair, and soft tissue repair.

The present invention provides a coated, prosthetic device comprising an implantable prosthetic device, wherein at least a portion of a surface of the implantable prosthetic device is coated with a tissue repair composition; wherein the tissue repair composition comprises a plurality of bone fragments and a carrier composition containing a carrier and one or more carrier compounds; and wherein the carrier consists essentially of one or more homogenized connective tissues.

The present invention also provides a method of coating a prosthetic device comprising providing an implantable prosthetic device, and applying a tissue repair composition to at least a portion of a surface of the implantable prosthetic device, wherein the tissue repair composition comprises a plurality of bone fragments and a carrier composition containing a carrier and one or more carrier compounds; and wherein the carrier consists essentially of one or more homogenized connective tissues.

The tissue repair composition of the present invention may be used for repairing or healing osseous defects, cartilage defects, and soft tissue defects. The tissue repair composition of the present invention may also be used for wound healing.

DESCRIPTION OF THE INVENTION

The present invention provides a carrier comprising one or more homogenized connective tissue. The carrier may consist of or consist essentially of one or more homogenized connective tissues. Examples of connective tissues that may be used in making the carrier of the present invention include but are not limited to fascia, tendons, ligaments, pericardium, cartilage, and mixtures thereof. The carrier of the present invention may serve as a vehicle for improved delivery of various biologically active agents and/or bone fragments that enhances their effectiveness at the target site. The target site may be a site of injury or an implant site.

The present invention also provides carrier compositions comprising a carrier consisting of or consisting essentially of one or more homogenized connective tissues and one or more additional carrier compounds. A carrier compound may be selected from the group consisting of antioxidants, water miscible polar organic compounds, water, natural polymers, synthetic polymers, antibiotics, antiviral agents, polysaccharides, extracellular matrix and a combination thereof.

Examples of antioxidants include but are not limited to aminoguanidine, ascorbic acid and salts thereof, phytic acid, tocols, isoflavones, vitamin A, β-carotene, selenium, zinc, copper, enzyme superoxide dismutase and its mimetics, or a combination thereof. The ascorbic acid may be L-ascorbic acid and salts thereof. Examples of tocols include tocopherols and tocotrienols. Examples of isoflavones include soy isoflavones. Selenium may be organic or inorganic selenium. The antioxidant in the carrier composition may be a radioprotectant, such as amino guanidine.

Examples of water miscible polar organic compounds include but are not limited to glycerol and ethanol. The water miscible polar organic compounds may be water replacement agents, such as glycerol.

The extracellular matrix may be extracted from animal tissues.

Biologically active agents used for repairing and/or regenerating tissues may be added to the carrier composition. Examples of these agents include but are not limited to bone fragments, blood, blood products, bioactive factors, and/or cells.

The bone fragments may include a plurality of naturally occurring bone fragments, a plurality of synthetic bone fragments, or a combination thereof. The bone fragments may be demineralized bone fragments, non-demineralized bone fragments, or a combination thereof Examples of demineralized bone fragments include demineralized bone particles and/or fibers. Examples of non-demineralized bone fragments include non-demineralized cancellous or cortical bone particles and/or fibers.

The blood products included in the carrier composition may include bone marrow aspirate (BMA), plasma, platelets, plasma rich platelet (PRP), red blood cells, granulocytes, and/or clotting proteins, such as Factor VIII and Factor IX.

Certain embodiments of the present invention are directed to compositions, such as carrier compositions and tissue repair compositions, and methods of preparing the same. The compositions of the present invention may be in the form of a fluid injectable gel, a fluid injectable paste, a putty, or a rehydratable freeze-dried paste. Some embodiments of the present invention may be used in clinical applications, such as spinal procedures, orthopedic procedures, craniomaxillofacial procedures, and dental procedures. Some embodiments of the present invention may be used to treat osseous defects, wounds, cartilage defects, and soft tissue defects.

Some embodiments of the present invention are directed to tissue repair compositions having a carrier consisting or consisting essentially of one or more homogenized connective tissues, and a plurality of bone fragments. In certain embodiments, the plurality of bone fragments includes demineralized bone fragments, non-demineralized bone fragments, synthetic bone fragments, or a combination thereof. In some embodiments, synthetic bone fragments may contain ceramic material, hydroxyapatite, calcium phosphate, calcium sulfate, calcium carbonate or a combination thereof. The tissue repair compositions may further include one or more biologically active agents such as blood products, bioactive factors, or cells. The cells may be mesenchymal stem cells, embryonic stem cells, progenitor cells, differentiated cells, undifferentiated cells, and/or induced pluripotent stem cells.

In certain aspects of the present invention, the compositions of the present invention may include at least one water miscible polar organic solvent. The water miscible polar organic solvent, for example glycerol and ethanol, may also be a water-replacement agent. In some aspects of the present invention, the compositions may include at least one radioprotectant (i.e., aminoguanidine, among others). In some embodiments, the compositions may include a polymer. In certain embodiments of the present invention, the tissue repair composition may be freeze-dried.

Some embodiments of the present invention are directed to tissue repair compositions having a plurality of bone fragments and a carrier composition. The bone fragments used in the present invention include but are not limited to demineralized and non-demineralized bone fragments, synthetic bone fragments, or a combination thereof. The bone fragments may be naturally occurring bone fragments or synthetic bone fragments. The bone fragments may also be bone particles or bone fibers. The carrier composition may include a carrier compound and a carrier. The carrier may include one or more homogenized connective tissue. The carrier may consist of or consist essentially of one or more homogenized connective tissue. The bone fragments may be bone particles or bone fibers, in certain embodiments. In some embodiments, bone fragments may be derived from allogenic cortical or cancellous bone or xenogenic cortical or cancellous bone. Demineralized bone fragments may, in certain embodiments, have less than about 8 wt % residual calcium or between about 0% to 4% residual calcium. The tissue repair composition may include between about 5 wt % and about 90 wt % demineralized bone fragments, in some embodiments.

Certain embodiments of the present invention are directed to tissue repair compositions including a carrier having homogenized fascia, a plurality of bone fragments, one or more radioprotectants, and one or more water miscible polar organic compounds.

The present invention provides methods of preparing a carrier composition and a tissue repair composition. The methods of the present invention involve preparing a connective tissue homogenate, mixing the connective tissue homogenate with a carrier compound to obtain a carrier composition, combining the carrier composition with at least one of a plurality of bone fragments. In some embodiments, the combining step further includes combining the carrier composition and the plurality of bone fragments with a water miscible polar organic solvent. The water miscible polar organic solvent may be a water replacement agent. Certain methods of the present invention involve freeze-drying the carrier composition before or after the combining step but prior to implantation. Some aspects of the present invention involve freeze-drying the carrier and/or the plurality of bone fragments before the combining step. Certain methods may further include at least one of a bone fragmentation step; a connective tissue fragmentation step; a heating step; a connective tissue homogenization step; an optional bone demineralization step; a selecting of bone fragments, demineralized, non-demineralized, and/or synthetic bone fragments of a particular size range step; a freeze-drying step; a packaging step; a sterilization step; and a rehydrating step.

Certain methods include combining a plurality of bone fragments and a carrier composition to obtain a tissue repair composition. Optionally, other biologically active agent also be added to such a tissue repair composition.

Certain embodiments of the present invention are directed to prosthetic devices including, an implantable prosthetic device, and a coating directly adjacent to at least a portion of a surface of the implantable prosthetic device. The coating includes at least one tissue repair composition including (a) a plurality of bone fragments and/or (b) a homogenized connective tissue.

Some embodiments of the present invention are directed to a method of coating a prosthetic device including, providing an implantable prosthetic device, and applying at least one tissue repair composition to at least a portion of a surface of the implantable prosthetic device. The tissue repair composition is as described herein.

Certain aspects of the present invention are directed to methods of promoting tissue repair or regeneration involving applying a tissue repair composition as described above to a damaged tissue to promote repair or regeneration of the tissue. The tissue may be an osseous tissue, a cartilage, or a soft tissue. Examples of soft tissues include tendons, ligaments, muscles, synovium, blood vessel, and nerves. Some embodiments of the present invention are directed to methods of inducing bone or cartilage formation involving applying the tissue repair composition as described above to an implant site to induce bone or cartilage formation. The tissue repair composition of the present invention may also be used to heal or repair wounds or tissue defects.

Some embodiments of the present invention are directed to tissue repair kits that include a carrier having at least one homogenized connective tissue, and at least one of a plurality of bone fragments. Certain embodiments of the present invention are directed to methods of using a tissue repair kit to produce a tissue repair composition. In the present application, the term "connective tissue" refers to mesodermally derived tissue that may be more or less specialized, and that is, at least in part, made up of fibers. Most of the connective tissues contemplated in the present invention are less specialized tissues that are rich in extracellular matrix (i.e., collagen, proteoglycan, among others), and that surround other more highly ordered tissues and organs. A relatively, more specialized tissue contemplated in the present invention is cartilage. Varieties of connective tissue that may be used in the present invention include: loose; adipose; dense, regular or irregular; white fibrous; elastic; and cartilage. Connective tissue may be classified according to concentration of fibers as loose (areolar) and dense, the latter having more abundant fibers than the former. Connective tissues may be obtained from vertebrates. In some embodiments, the tissues may have human, bovine, equine, porcine, ovine, caprine, or piscene origins, among others. Connective tissues may also be the product of biotechnological methods (i.e., production of tissue engineered connective tissues using cell culture methods).

Specific examples of connective tissues that may be used in certain embodiments of the present invention include, at least, fascia, tendons, ligaments, pericardium, cartilage, and mixtures thereof. Different types of fascia that may be used in certain embodiments of the present invention include: fascia lata, fascia adherens, fascia brachii, fascia axillaris, antebrachial fascia, abdominal fascia, internal fascia, fascia iliaca, fascia profunda, clavipectoral fascia, fascia cribosa, crucial fascia, deltoid fascia, dorsal deep fascia, pelvic fascia, fascia cruris, lumbar fascia, and pectoral fascia, among others. "Crudely fragmented connective tissue" refers to connective tissue that has been sliced, ground, carved, chipped, chopped, minced, cut, dissected, rent, ripped, sectioned, snipped, diced, shaved, comminuted, or trimmed into fragments having an average diameter greater than about 50 microns and less than about 0.5 cm (i.e., having cut dimensions of approximately 0.5×0.5 cm), and thickness appropriate to the tissue being crudely fragmented. In some embodiments, the crude fragments may not be of uniform size.

A "carrier" is a matrix or substance that may serve as a vehicle to improve the delivery and maintain the effectiveness of biologically active agents. An example of a carrier that is used in the present invention is homogenized connective tissues. The carrier of the present invention may comprise one or more homogenized connective tissues. The carrier may consist essentially of one or more homogenized connective tissues.

A "carrier compound" is a compound that is added to a carrier. Examples of such compounds include but are not limited to antioxidants, water miscible polar organic compounds, water, natural polymers, synthetic polymers, antibiotics, antiviral agents, polysaccharides, or extracellular matrix. The antioxidant may be a radioprotectant.

"Homogenized connective tissue" or "connective tissue homogenate" contains connective tissue that has been reduced to particles that are uniformly small and evenly distributed. Homogenized connective tissue may optionally include at least one of water, aqueous solutions, water-replacement agents, or water miscible polar organic solvents, in addition to the particles. The homogenized connective tissues used in methods of the present invention include particles having an average diameter of less than about 50 microns. In some embodiments, the homogenized connective tissue may be prepared by shear-induced shredding of a composition including connective tissue, and optionally, at least one of water, an aqueous solution, a water-replacement agent, and a water miscible polar organic solvent. A conventional blender may be used in preparing the homogenized connective tissue, in certain embodiments.

"Osseous tissue" is meant to refer to bone tissue, tissue resembling bone, and tissue capable of forming bone. The term "bone" or "bone tissue" is intended for the purposes of the invention to refer to autograft bone, allograft bone, and xenograft bone. Such bone includes any bone from any source, including: bone from a living human donor, bone from a human cadaveric donor, and bone from an animal. The bone may include cortical bone and/or cancellous bone and/or cortico-cancellous bone. The term "bone fragment," as used in the present application refers to ground bone, pulverized bone, bone cubes, bone chips, bone strips, bone particles, bone rods, and bone fibers. Bone fragments may be "bone particles" or "bone fibers," in some embodiments of the present invention. "Bone particle" refers to a piece of bone having an average diameter of between about 125 microns and about 4 mm. "Bone fiber" refers to a filament or thread of bone having an average thickness of between about 0.1 mm and about 1.4 mm and an average width of between about 0.3 mm and about 2.5 mm. Fibers can be of varying lengths. In certain embodiments, a bone fiber can have an average length of between about 1.0 mm and about 100 mm. In certain embodiments, bone fiber contains lamellae in the shape of threads or filaments having a median length to median thickness ratio of about 10:1. "Bone rods" may have an average width of between about 0.5 mm and about 5 mm, and an average length of between about 1 mm and about 100 mm. "Bone cubes" may have an average volume of between about 0.001 mm$^3$ and about 1000 mm$^3$.

Bone fragments used in the present invention may be demineralized or non-demineralized. "Demineralized bone," as used in the present application refers to bone having less than about 8 wt % residual calcium. Demineralization involves treating the surface of a bone tissue to remove a surface layer of its inorganic mineral hydroxyapatite material leaving the mechanical properties of the organic phase of the bone constructs substantially unchanged. The level of demineralization of a bone tissue is defined by the amount (wt %) of residual calcium found in the demineralized bone. In some embodiments, the demineralized bone may contain physiologically active levels of growth and differentiation factors (i.e., bone morphogenetic proteins (BMPs)). "Non-demineralized bone" as used in the present application refers to bone that has not been treated to remove minerals present such as, for example, hydroxyapatite.

Bone fragments include "synthetic bone fragments." The synthetic bone fragments used in the present composition may be composed of one or more of ceramic, hydroxyapatite, calcium phosphates, calcium sulfates, bioactive glass, and calcium carbonates, among others. The synthetic bone fragments may be in the form of a powder, cubes, chips, strips, particles, rods, and fibers. The synthetic bone fragments may have an average diameter of between about 125 microns and about 2000 microns. The synthetic bone fibers may have an average width of between about 0.1 mm and about 2 mm, and an average length of between about 0.3 mm and about 100 mm. The synthetic bone-alternative rods may have an average width of between about 0.5 mm and about 5 mm, and an average length of between about 1 mm and about 100 mm. The synthetic bone alternative cubes may have an average volume of between about 0.001 mm$^3$ and about 1000 mm$^3$.

The bone fragments of used in the present invention may include a combination of natural and synthetic bone fragments. The bone fragments used in the present invention may also include a combination of demineralized and non-demineralized bone fragments.

In the present application, the term "gel" refers to a jelly-like, thick, soft, partly liquid substance. A gel of the present invention may be extruded through a syringe. The syringe may have a needle of about 13 gauge. "Paste," as used in the present application refers to a soft, moist, substance having a consistency between a liquid and a solid. A paste of the present invention is less solid than a putty and more solid that a gel, and in some embodiments may be injectable.

"Putty" refers to a dough-like/clay-like tissue repair composition of the present invention. During application the substance may be beaten or kneaded to the consistency of dough, and molded into a shape closely approximating that of the implant site.

"Injectable" refers to the ability of certain tissue repair compositions of the present invention to be introduced at an implant site under pressure (as by introduction using a syringe). An injectable composition of the present invention may, for example, be introduced between elements or into a confined space in vivo (i.e., between pieces of bone or into the interface between a prosthetic device and bone, among others).

"Syringe" refers to any device that may be used to inject or withdraw flowable tissue repair compositions of the present invention, including certain gels and pastes, among others.

"Flowable" refers to the characteristic of a composition that permits it to be made to fit closely by following the contours of a site. Flowable compositions may be fluid, malleable, plastic, and/or pliable.

"Allogenic tissue" refers to a tissue from a donor that is implanted into a recipient of the same species. Allograft tissue is widely used in orthopedic, neuro-, maxillofacial, podiatric, and dental surgery. The tissue is valuable because it is strong, biointegrates in time with the recipient patient's tissue and may be shaped or reconfigured to fit the specific surgical defect. Contrasted to most synthetic absorbable or nonabsorbable polymers or metals, allograft tissue is biocompatible and integrates with the surrounding tissues. Allograft bone occurs in two basic forms: cancellous and cortical.

"Xenogenic tissue" refers to a tissue from one species that is implanted into a recipient of another species.

"Cortical bone," as used in the present application, refers to the compact bone of the shaft of a bone that surrounds the medullary cavity. Cortical bone is a highly dense structure made up of triple helix strands of collagen fiber, reinforced with hydroxyapatite. The cortical bone is a compound structure and is the primary load bearing component of long bones in the human body. The hydroxyapatite component is responsible for the high compressive strength of the bone while the collagen fiber component contributes in part to torsional and tensile strength.

Trabecular bone is of similar composition to cortical bone and is the primary structural component of "cancellous bone" and refers to adult bone having mineralized regularly ordered parallel collagen fibers organized differently than in the lamellar bone of the shaft of adult long bones. Cancellous bone is generally found in the end of long bones surrounded by cortical bone. Cancellous bone has spicules that form a latticework, with interstices filled with bone marrow. It may also be referred to as a trabecular bone, or spongy bone.

"Aseptic" as a term can be applied to both products and processes and is generally applied to the control or reduction in microbial bioburden. Tissues processed "aseptically" are tissues processed using sterile instruments, and special environmental surroundings (including for example "clean room technologies"). Aseptic tissues make reference to tissues that are "culture negative," where culture negative makes reference to the use of representative pieces of tissue that have been or will be processed for an assessment of the presence of microorganisms. The level of sensitivity of the microbiological test method(s), and hence a better definition of "culture negative," is generally predetermined by assessing for interference in the detection of such microorganisms (sometimes referred to as bacteriostasis and fungistasis, B&F, testing).

"Sterile" makes reference to a definition such as contained in the Code of Federal Regulations (21 CFR) where the probability of a culturable microorganism being present on a processed sample is equal to or less than 1 in one million, i.e., a Sterility Assurance Level, or SAL, of $1 \times 10^{-6}$.

An "osseous defect" is generally defined by one skilled in the art as being an imperfection or void in an osseous tissue, which is of sufficient physical dimensions as to not heal spontaneously. Hence, the use of materials generally referred to as "bone void fillers" are utilized clinically to aid or improve healing of the osseous defect. Certain compositions of the present invention can be used as bone void fillers. Osseous defects may include: fractures, cracks, and osteosarcomas (bone cancer lesions), among others. Bone void fillers may be used to fill a gap between a prosthetic device and bone; between pieces of bone; and between two different prosthetic devices. For example, a bone void filler can be used to fill the space between a hip replacement and a bore in a bone into which the hip replacement has been inserted.

The tissue repair composition may contain one or more "bioactive factors", "bioactive compounds", "bioactive components" or "bioactive materials." Examples of bioactive factors, bioactive compounds, bioactive components, or bioactive materials included in the compositions of the present invention may be an osteoinductive factor, a chondrogenic factor, a cytokine, a mitogenic factor, a chemotactic factor, a transforming growth factor (TGF), a fibroblast growth factor (FGF), an angiogenic factor, an insulin-like growth factor (IGF), a platelet-derived growth factor (PDGF), an epidermal growth factor (EGF), a vascular endothelial growth factor (VEGF), a nerve growth factor (NGF), a neurotrophin, a bone morphogenetic protein (BMP), osteogenin, osteopontin, osteocalcin, cementum attachment protein, erythropoietin, thrombopoietin, tumor necrosis factor (TNF), an interferon, a colony stimulating factor (CSF), or an interleukin, among others. The bioactive factor may be a BMP, PDGF, FGF, VEGF, TGF, insulin, among others. Examples of BMPs include but are not limited to BMP-2, BMP-3, BMP-4, BMP-5, BMP-6, BMP-7, BMP-8, BMP-9, BMP-10, BMP-11, BMP-12, BMP-13, BMP-14, and BMP-15. The bioactive factor included in the tissue repair composition may be a combination of various bioactive factor.

Certain embodiments of the present invention are directed to compositions having a carrier including at least one homogenized connective tissue, and at least one of a plurality of bone fragments. Some embodiments of the present invention are directed to compositions having a plurality of bone fragments and a carrier. The carrier may include at least one homogenized connective tissue. In certain embodiments, the carrier may consists of or consist essentially of at least one connective tissue. In some embodiments, the composition may be a tissue repair composition and may be safely used in repairing damaged osseous tissues (e.g., damaged bone) in an implant patient. The tissue repair composition may, in some embodiments, be biocompatible, osteoinductive, and/or osteoconductive, such that it may ultimately be remodeled to a mineralized, hard tissue at the application site in vivo. In certain embodiments, the tissue repair compositions may further include at least one of water, an aqueous solution, a water-replacement agent, a water miscible polar organic solvent, and other components described below. The tissue repair composition may include materials that improve handling or functional characteristics post-implantation. In some embodiments, bone and connective tissue may be obtained from the same donor source (i.e., a single human cadaver donor). The formulation of the inventive tissue repair composition may be highly reproducible. In certain embodiments, the tissue repair composition may be aseptic or sterile.

The composition may be in the form of a gel, a paste, a putty, or a freeze-dried substance that can be rehydrated to produce a paste or a putty. In certain embodiments, a freeze-dried substance may be rehydrated with a bodily fluid (i.e., blood or bone marrow aspirate, among others). In some embodiments, the gel or paste may be injectable, and the gel or paste may be extrudable through a syringe and/or a syringe having at least a 13 gauge tube/needle coupled thereto. Certain gels and pastes may be used for accurate delivery of the tissue repair composition into narrow junctions with minimal surgical damage to surrounding tissue at the implant site. Some of the tissue repair compositions of the present invention may be moldable. Tissue repair compositions of the present invention may be cast into a shaped form, in certain embodiments.

In some embodiments, each of (a) the bone fragments demineralized, non-demineralized, synthetic, or a combination thereof and (b) the homogenized connective tissue of the inventive composition may include materials derived from allogenic or xenogenic sources. In certain embodiments, bone and connective tissues obtained from vertebrate species, for example human, bovine, porcine, equine, ovine, caprine, and piscene sources may be used to prepare bone fragments and carrier. The plurality of bone fragments may include more than one type of bone tissue (e.g., cancellous, cortical, or cortico-cancellous bone, and demineralized or non-demineralized bone), and the connective tissue that is homogenized to make the carrier may include more than one type of connective tissue (i.e., fascia and tendon). The plurality of bone fragments may include bone from a single donor source, or from multiple donor sources, and the homogenized connective tissue may also include tissue from a single donor source, or from multiple donor sources.

For preparation of the tissue repair compositions of the present invention, the carrier having the connective tissue homogenate and the bone fragments are combined together.

In some embodiments, the tissue repair composition may include between about 5 wt % and about 90 wt %; between about 20 wt % and about 80 wt %; and between about 30 wt % and about 50 wt % bone fragments. Certain tissue compositions of the present invention that are in the form of a gel or paste may include between about 15 wt % and about 30 wt % bone fragments, while certain compositions of the present invention that are in the form of a putty may include between about 25 wt % and about 40 wt % of the bone fragments. In some embodiments, the tissue repair composition may be in the form of a freeze-dried product that may be rehydrated to produce a paste or a putty, which may include between about 35 wt % and about 70 wt % bone fragments.

In certain embodiments, the tissue repair composition may include demineralized bone fragments having less than about 8 wt %, less than about 4 wt % residual calcium, from about 0.5 wt % to about 4 wt % residual calcium, or from about 1 wt % to about 4 wt % residual calcium. The tissue repair composition may include demineralized bone fragments having between about 0 wt % and about 8 wt %, about 0.5 wt % and about 6 wt %, about 0.5 wt % and about 4 wt %, or about 2 wt % and 4 wt % residual calcium, in some embodiments.

In certain embodiments, the tissue repair composition may include between about 0.25 wt % and about 80 wt %, or about 0.5 wt % and about 10 wt % of the connective tissue homogenate. The connective tissue homogenate may include one or more connective tissues that have been homogenized. The amount of homogenized connective tissue used in a tissue repair composition may be used to adjust the viscosity and gelation characteristics of the composition.

The plurality of bone fragments may include at least one of non-demineralized bone particles, non-demineralized bone fibers, demineralized bone particles, and demineralized bone fibers, in some embodiments. The bone fragments may include materials derived from allogenic or xenogenic sources. The bone fragments may be derived from cortical bone or cancellous bone. In certain embodiments, the plurality of bone fragments includes at least one of non-demineralized allogenic cortical bone particles, non-demineralized xenogenic cortical bone particles, non-demineralized allogenic cancellous bone particles, non-demineralized xenogenic cancellous bone particles, demineralized allogenic cortical bone particles, demineralized xenogenic cortical bone particles, demineralized allogenic cancellous bone particles, and demineralized xenogenic cancellous bone particles.

Certain tissue repair compositions of the present invention may include bone particles. Bone particles may be prepared from cleaned and disinfected bone fragments that have been freeze-dried and ground/milled/fractured into bone particles. Bone particles may be selected by, for example, using sieving devices (i.e., mesh sieves) commercially available to obtain particles within a desired size range. Such bone particles may have an average diameter of between about 125 microns and about 4 mm; between about 125 microns and about 2000 microns; between about 710 microns and about 2 mm; between about 125 microns and about 500 microns; between about 125 microns and about 850 microns; or between about 250 microns and about 710 microns. Certain embodiments of the present invention may include demineralized bone powder that is commercially available. For example, a suitable demineralized bone powder that is widely and reliably available is produced by LifeNet Health, Virginia Beach, Va.

Some tissue repair compositions of the present invention may include bone fibers. Fiber bone may be produced as described in U.S. patent application Ser. No. 10/606,208, published as publication number 2004/0059364, which is hereby incorporated by reference in its entirety. In certain embodiments, the bone fibers may have an average thickness of between about 0.1 mm and about 0.3 mm and an average width of between about 0.1 mm and about 2 mm; about 0.3 mm and about 1.0 mm; or about 0.3 mm and about 2.5 mm. The length of the fibers may vary. In some embodiments, the bone fibers may have an average length of between about 0.3 mm and about 100 mm. Bone rods in certain embodiments may have an average width of between about 0.5 mm and about 5 mm, and an average length of between about 1 mm and about 100 mm. Bone cubes in some embodiments may have an average volume of between about 0.0001 $mm^3$ and about 1000 $mm^3$.

Any demineralization processes known in the art, may be used to prepare demineralized bone fragments. Examples of such processes are described in U.S. Pat. Nos. 6,830,763; 6,534,095; 6,305,379; 6,189,537; 5,531,791; and 5,275,954. In some embodiments, the demineralization process begins by producing bone particles having an average diameter size range of between about 0.1 mm and about 5 mm, about 0.2 mm and about 2 mm, about 0.25 and 1 mm, or about 0.25 mm and about 0.75 mm, or by producing bone fibers having an average dimension of 0.1 mm to 0.3 mm thick and an average width of about 0.3 mm to about 1 mm. The fragments may then be treated by such processes as are described in U.S. Pat. Nos. 5,556,379; 5,797,871; 5,820,581; 5,976,104; 5,977,034; 5,977,432; and 6,024,735, which are hereby incorporated by reference in their entirety. If the bone to be processed into fragments has not been previously cleaned and disinfected, they may be cleaned and disinfected by the use of detergents, hydrogen peroxides, antibiotics, and alcohols to affect a removal of associated tissues such as bone marrow and cellular elements. Following a cleaning and disinfection, these fragments (i.e., particles and fibers) may be demineralized by exposure to dilute hydrochloric acid, such as are known in the art, to affect a removal/reduction of the mineral component of the bone fragments (i.e., particles and fibers). Such additional processing may, in some instances, inactivate potential viral contamination (i.e., HIV and hepatitis viruses, among others).

In certain embodiments in which non-demineralized or demineralized bone fragments are to be used later, they may be conveniently stored by freeze-drying, which may maintain the activity of their bioactive components (i.e., BMPs, among others). If the bone fragments are to be used later, in some embodiments, the acidic demineralization solution may be removed from the bone using aqueous or polar (miscible with water) organic solutions, for example deionized/distilled endotoxin-free water, saline solutions, acetone, alcohol(s), and dimethylsulfoxide, in order to minimize elevated levels of salts in the freeze-dried bone.

Some tissue repair compositions of the present invention may include synthetic bone fragments. Such synthetic bone fragments may include fragments having an average diameter of between about 125 microns and about 2000 microns, or between about 250 microns and about 710 microns. The synthetic bone fragments may include synthetic bone fibers having an average thickness of between about 0.1 mm and about 0.3 mm and an average width of between about 0.1 mm and about 2 mm, or about 0.3 mm and about 2.5 mm. The length of the fibers may vary. In some embodiments, the bone-alternative fibers may have an average length of between about 0.3 mm and about 100 mm. Synthetic bone fragments may include bone rods in certain embodiments having an average width of between about 0.5 mm and about 5 mm, and an average length of between about 1 mm and about 100 mm. Synthetic bone fragments may include bone cubes in some embodiments having an average volume of between about 0.0001 mm³ and about 1000 mm³.

Compositions of the present invention may contain a carrier having a homogenized connective tissue. In certain embodiments, the carrier in the composition may consist of or consist essentially of homogenized connective tissue. In other embodiments, the composition may contain a carrier along with one or more other components. The components may be a carrier compound and/or a biologically active agent, such as bone fragments. In some embodiments, the carrier may include a biocompatible liquefied form of connective tissue (i.e., liquefied human connective tissue) that when combined with bone fragments, has suitable viscosity so as to be injectable through large gauge applicators, while largely remaining at the implant site. The carrier may promote cellular infiltration and retain the bone fragments at the site of application, without being cytotoxic. The carrier may promote such cellular infiltration by providing a molecular matrix for cell migration. In some embodiments, the carrier may be freeze-dried prior to combining with other components. In certain embodiments, the carrier includes homogenized fascia.

In some embodiments, the homogenized connective tissue may be prepared from allogenic or xenogenic tissue. Such connective tissue may be obtained from a human donor or an animal (i.e., bovine donor, porcine donor, etc.). Connective tissue may be obtained relatively economically. Varieties of connective tissue that may be used in certain embodiments of the present invention include: areolar or loose; adipose; dense, regular or irregular; white fibrous; elastic; and cartilage. Specific examples of connective tissues that may be used in certain embodiments of the present invention include, at least: fascia, tendons, ligaments, pericardium, cartilage, and combinations thereof. Different types of fascia that may be used in some embodiments of the present invention include: fascia lata, fascia adherens, fascia brachii, fascia axillaris, antebrachial fascia, abdominal fascia, internal fascia, fascia iliaca, fascia profunda, clavipectoral fascia, fascia cribosa, crucial fascia, deltoid fascia, dorsal deep fascia, pelvic fascia, fascia cruris, lumbar fascia, and pectoral fascia, among others. For practical reasons of availability during procurement and amount of fascia available, fascia lata from the anterior portion of the upper leg may be used in certain embodiments.

Homogenized connective tissue may be prepared by methods involving, cleaning and disinfecting connective tissue, and removing extraneous tissues associated with the connective tissue. Connective tissues may be cut into small pieces to produce crudely fragmented connective tissue, and optionally triturated and washed with distilled/deionized endotoxin-free water and/or an aqueous solution (i.e., isotonic saline, among others). In processing, multiple "washes" may be affected using volumes of aqueous solution that are 10 times the approximated volume of the tissue being processed, in some embodiments. It would be obvious to one skilled in the art that the use of three such processing steps would affect an approximate 1:1000 dilution of associated solubilizable elements rendering the tissue essentially free from such solubilizable elements.

Connective tissue may be treated and homogenized at temperatures sufficient to produce a flowable homogenized connective tissue, in certain embodiments. The homogenized connective tissue may include connective tissue that has been reduced to particles that are uniformly small and evenly distributed. Homogenized connective tissue and/or the carrier may optionally include at least one of water, aqueous solutions (i.e., isotonic saline), water-replacement agents, and water miscible polar organic solvents in addition to the connective tissue particles. In some aspects, the homogenized connective tissue may include gelatin. The homogenized connective tissues used in methods of the present invention may include particles having an average diameter of less than about 50 microns, less than about 20 microns, or less than about 50 microns and greater than about 5 microns. In some embodiments, the homogenized connective tissue and optionally, at least one of a water-replacement agent, a water miscible polar organic solvent, water, and an aqueous solution, may be prepared by shear-induced shredding of connective tissue. A conventional blender may be used in preparing the homogenized connective tissue, in certain embodiments.

In some embodiments of the present invention, connective tissue homogenate and/or the carrier will retain large and small molecular weight macromolecules, including hyaluronate which is known to play a role in cell migration (Toole, B. P. and Trelstad, R. L., 1971, Develop. Biol. 26:28-35; Docherty, R., et al., 1989, J. Cell. Sci. 92:263-270) and has been implicated in facilitating fibril formation which promotes gelation (Tsunenaga, M., et al., 1992, Connect. Tiss. Res. 28:113-123). The connective tissue homogenate and/or carrier may have excellent histocompatibility and elicit minimal antibody formation or immunological rejection, in certain embodiments. Keeping this in mind, the homogenized connective tissue may be made acellular, using methods known in the art, prior to homogenization, and methods of making such tissues acellular are described in U.S. Pat. Nos. 6,734,018 and 6,743,574; which are hereby incorporated by reference in their entirety.

In certain embodiments, the homogenized connective tissue may be acellular or cellular. An acellularization process used to prepare homogenized connective tissue of the present invention may be performed without damage to matrix and/or tissue structure, in some embodiments. Mechanical strength of a connective tissue may reside in the matrix structure of the tissue. The matrix structure may include collagens, hyaluronins, elastins, mucopolysaccharides and proteoglycans, among other components. An example of an acellularization method for use with soft tissues is described in U.S. Pat. Nos. 6,734,018 and 6,743,574, which are hereby incorporated by reference in their entirety. Connective tissue that is acellularized may have a thickness that does not exceed about 8 mm, about 6 mm, about 4 mm, about 2 mm, about 1 mm, or about 0.2 mm, in certain embodiments. Acellularization processing may be altered to accommodate the thicker tissues.

The compositions of the present invention may contain additional elements such as antioxidants, polymers, bodily fluids (i.e., blood or bone marrow aspirate, among others), water, aqueous solutions, water-replacement agents, water miscible polar organic solvent, surfactants, bioactive factors, antibiotics (i.e., penicillin), antiviral agents (i.e., Triton X-100, Nonidet P40, N-lauroyl sarcosinate, Brij-35, and peroxide generating agents), antitumor agents, analgesics, immunosuppressive agents (i.e., bovine intestinal alkaline phosphatase), permeation enhancers (i.e., fatty acid esters, such as the laurate, myristate and stearate monoesters of polyethylene glycol), nucleic acids, mesenchymal elements, gelation enhancing compounds (i.e., hyaluronic acid, chondroitin sulfate, dermatin sulfate, carboxymethylcellulose, methylcellulose, polyethylene glycol, or glycosamino glycans), or autogenously derived osteoprogenitor cells and/or osteoblast cells, and other biologically active agents. Some compounds may fall into more than one category of additional elements. For example, glycerol may be both a water-replacement agent and a water miscible polar organic solvent. As another example, Triton X-100 may be both a surfactant and an antiviral agent.

Antioxidants such as radioprotectants may be included in the compounds of the present invention. Radioprotectants may provide protection against certain undesirable effects of ionizing radiation. In some embodiments, a composition of the present invention, such as a tissue repair composition, may be subjected to irradiation, and the tissue repair composition may include at least one radioprotectant, for example aminoguanidine, that reduces undesirable effects (i.e., poor handling characteristics among others) that may result from such irradiation. In some embodiments, a radioprotectant may be biocompatible, and that the radioprotectant itself may not introduce undesirable properties into a tissue repair composition. In certain embodiments of the present invention, the tissue repair composition may include a radioprotectant, and may be osteoinductive and biocompatible. In some embodiments, the tissue repair composition may include between 10 mM and about 500 mM radioprotectant(s).

Exemplary radioprotectants that may be used in some embodiments of the present invention include aminoguanidine, ascorbic acid and salts thereof, and phytic acid and salts thereof. In certain embodiments, the radioprotectant may be aminoguanidine at a concentration between about 10 mM and about 1M, or between about 10 mM and 100 mM in the tissue repair composition. In some embodiments of the present invention, the radioprotectant may be L-ascorbic acid salt at a concentration of between about 50 μM and about 1M, between about 150 mM and about 500 mM, or between about 250 mM and about 500 mM in the tissue repair composition. In certain embodiments, the radioprotectant may be L-ascorbic acid 2-phosphate sesquimagnesium salt at a concentration of between about 50 μM and about 1M, between about 50 μM and about 500 mM, or between about 50 mM and about 250 mM. In some embodiments, the radioprotectant may be phytic acid at a concentration of between about 100 μM and about 100 mM in the tissue repair composition. A radioprotecant may be added to the composition of the present invention, such as a tissue repair composition, or a component of a composition at any point during processing before the composition or component is irradiated, in certain embodiments.

Polymers that may be used in certain tissue repair compositions of the present invention include natural polymers and synthetic polymers. In certain embodiments of present invention, a polymer in a tissue repair composition may be a polysaccharide, such as alginate, propylene glycol alginate, native or crosslinked chitosan, starch, agarose, chitin, cellulose and derivatives thereof (i.e., cellulose acetate, carboxymethyl cellulose, and methylcellulose, among others), xanthan gum, dextran, carrageenan, hyaluronic acid, chondroitin sulfate, locust bean gum, gum tragacanth, gum arabic, curdlan, pullulan, scleroglucan, or lower methoxyl pectin, among others. In some embodiments, a tissue repair composition of the present invention may include at least one of native or modified extracellular matrix, such as collagen, gelatin, hyaluronic acid, fibrin, MATRIGEL™ (BD Biosciences, San Jose, Calif.), human extracellular matrix (i.e., a chromatographically partially purified matrix extract derived from human placenta is available from BD Biosciences, San Jose, Calif.), proteoglycans, laminin, fibronectin, or elastin. In some embodiments, a tissue repair composition of the present invention may include heparin, polyethylene glycol, biotin, avidin, polymethylmethacrylate, polyurethane, acryloilmorpholine, N,N-dimethyl acrylamide, N-vinyl pyrrolidone, glycerol, sucrose octasulfate, hydroxyapatite, tetrahydrofurfuryl methacrylate, and polylactic acid. Some tissue repair compositions of the present invention may include cross-linkage or functionalization of hyaluronan, collagen, or alginate.

Water-replacement agents that may be used in certain embodiments of the present invention include glycerol (glycerin USP), adonitol, sorbitol, ribitol, galactitol, D-galactose, 1,3-dihydroxypropanol, ethylene glycol, triethylene glycol, propylene glycol, glucose, sucrose, mannitol, xylitol, meso-erythritol, adipic acid, proline, hydroxyproline, polyethylene glycol, alcohol, and lipids. Certain tissue repair compositions of the present invention include glycerol.

Examples of bioactive factors include: bone morphogenic proteins, transforming growth factor beta, fibroblast growth factor, insulin, vascular endothelial growth factor, and platelet derived growth factor, among others. In this respect, the invention includes other equivalent optional components readily known to those in the art.

Tissue repair compositions of the present invention may include a calcium phosphate and/or calcium sulfate mineral component to produce an osteoinductive/osteoconductive composition which will harden prior to or post implantation. Tissue repair compositions of the present invention may also include particulate hydroxyapatite, calcium phosphate, magnesium phosphate, calcium carbonate, as extenders of the compositions and as sources of mineral in subsequent induced new bone formation.

As described above, certain tissue repair compositions of the present invention may include a plurality of bone fragments and a carrier. The carrier may consist of or consist essentially of at least one homogenized connective tissue, and, optionally, one or more additional components. The carrier may consist essentially of one or more homogenized connective tissue. In some embodiments of the present invention, no water is added to the carrier/homogenized connective tissue. In certain carriers of the present invention, the weight ratio of the additional component(s) to the wet weight of homogenized connective tissue(s) may be from about 0.1:1 to about 12:1, or from about 0.5:1 to about 6:1. In some embodiments, the at least one additional component may be water, an aqueous solution, alginate, propylene glycol alginate, native or crosslinked chitosan, starch, cellulose and derivatives thereof, xanthan gum, dextran, carrageenan, hyaluronic acid, chondroitin sulfate, locust bean gum, gum tragacanth, gum arabic, curdlan, pullulan, scleroglucan, lower methoxyl pectin, native or modified collagen, gelatin, agarose, modified hyaluronic acid, fibrin, chitin, biotin, avidin, Matrigel™, human extracellular matrix, proteoglycans, laminin, fibronectin, elastin, heparin, polyethylene glycol, polymethylmethacrylate, polyurethane, acryloilmorpholine, N,N-dimethyl acrylamide, N-vinyl pyrrolidone, glycerol, sucrose octasulfate, hydroxyapatite, tetrahydrofurfuryl methacrylate, or polylactic acid. In certain embodiments of the present invention, the additional component in a carrier may include a water-replacement agent or a water miscible polar organic solvent, as described above. In some embodiments, the additional component may be about 0% to about 100% water by weight, or about 0.1% to about 90% water by weight. Thus, if the additional component is water, it is 100% water by weight, and if the additional component is a 10 wt % glycerol solution, it is 90% water by weight.

Certain embodiments of the present invention are directed to tissue repair compositions including a carrier including homogenized fascia, a plurality of bone fragments, at least one radioprotectant, and at least one water-replacement agent or at least one water miscible polar organic solvent. In some embodiments, the carrier consists of homogenized fascia. In certain embodiments the bone fragments may be demineralized bone fragments, non-demineralized bone fragments, synthetic bone fragments, or a combination thereof. The bone fragments may be freeze-dried bone fragments in some embodiments of the present invention. In certain aspects of the present invention, the water-replacement agent may be glycerol. The radioprotectant may be aminoguanidine, and the tissue repair composition may include between about 10 mM and about 100 mM aminoguanidine, in some embodiments.

Some embodiments of the present invention are directed to tissue repair kits including: a carrier having at least one homogenized connective tissue, and at least one of a plurality of bone fragments. In certain aspects of the present invention, the carrier consists essentially of at least one homogenized connective tissue and a water-replacement agent. The carrier may be a freeze-dried carrier in some embodiments of the present invention. In certain embodiments, the bone fragments in the kit may be freeze-dried. In some tissue repair kits of the present invention, the bone fragments include a water-replacement agent. In some embodiments, the water-replacement agent may be glycerol.

In some embodiments, the tissue repair composition or components of a tissue repair composition, and optionally means for applying a tissue repair composition (i.e., syringe or spatula) to an implant site may be provided in a unitary kit. In other embodiments, the bone fragments, the connective tissue homogenate, and/or the carrier may be prepared under sterile conditions and stored separately, or mixed and stored together, for later use. To facilitate clinical usage of described tissue repair compositions, the bone fragments and/or the bone-alternative fragments, and the carrier/connective tissue homogenate may be packaged separately in different forms and reconstituted and combined at the time of usage, in some embodiments. In other embodiments, the components may be combined to produce a tissue repair composition, which is then packaged, in a premixed format.

Certain embodiments of the present invention are directed to methods of using the tissue repair compositions, described above. Some methods of the present invention include combining the carrier and the plurality of bone fragments in a tissue repair kit to produce a tissue repair composition. In certain embodiments, the methods further include adding at least one of water, an aqueous solution, and a bodily fluid to at least one component of the kit (e.g., the carrier and/or the plurality of bone fragments), or a tissue repair composition prepared using the kit.

The premixed format provides the advantage of requiring minimal preparation by the individual clinician at the time of usage. In some embodiments, the tissue repair composition may be stored in an application means, such as a syringe, which will be used to apply the composition to an osseous defect site. The tissue repair composition may, for example, be stored in a 1 to 10 cc syringe that is capable of being coupled to a large gauge delivery tube/needle of appropriate length and inside diameter. In this regard, a delivery tube with an inside diameter of not less than 13 gauge is appropriate for the injection delivery into an implant site.

For on-site preparation, the carrier/homogenized connective tissue and bone may be provided in freeze-dried aliquots that are rehydrated just prior to being combined for use in clinical applications, in some embodiments. In some embodiments, the aliquots may be rehydrated with a bodily fluid (i.e., blood or bone marrow aspirate, among others). On-site preparation has the advantage of increasing the ability to vary the concentrations and quantities of the connective tissue homogenate and/or bone fragments used in preparation of the inventive tissue repair composition. Furthermore, on-site preparation permits the addition of optional components at the discretion of the clinician.

Certain embodiments of the present invention are directed to methods for the preparation of the tissue repair compositions described above. Such methods include combining a plurality of bone fragments and a carrier having a homogenized connective tissue. Certain inventive methods include combining bone fragments with a carrier such that the tissue repair composition produced between about 5 wt % and about 90 wt %; between about 20 wt % and about 80 wt %; and between about 30 wt % and about 50 wt % bone fragments. In some embodiments, the bone fragments and the carrier may be combined with at least one of the component, as described above. The methods may include packaging the inventive tissue repair compositions, in certain embodiments. In some embodiments, inventive methods of the present invention include providing at least one of bone tissue or bone tissue fragments and at least one connective tissue, and preparing bone fragments and homogenized connective tissue from the at least one bone tissue and the at least one connective tissue, as described above. Bone fragments may include at least one of bone particles and bone fibers from bone tissue. Bone fragments may include demineralized bone fragments, non-demineralized bone fragment, synthetic bone fragments, or a combination thereof. Some methods of preparing the tissue repair compositions of the present invention may include the production of particles or fibers from bone tissue, as discussed above. Bone fragments may be demineralized, as described above, in certain embodiments. The bone fragments may be demineralized to have less than about 8 wt % residual calcium, less than about 4 wt % residual calcium, from about 0.5 wt % to about 4 wt % residual calcium, or from about 1 wt % to about 4 wt % residual calcium. The bone fragments may be demineralized to have between about 0 wt % and about 8 wt %, about 0.5 wt % and about 6 wt %, about 0.5 wt % and about 4 wt %, or about 2 wt % and about 4 wt % residual calcium, in some methods of the present invention. Certain methods of the present invention may include freeze-drying bone fragments. In some embodiments, the bone fragments may be freeze-dried to a point such that the freeze-dried fragments have an average residual moisture of less than about 10 wt %, or less than about 5 wt %. In some embodiments, freeze-dried bone fragments may be rehydrated before use in preparing the tissue repair compositions of the present invention.

Certain methods for producing the compositions of the present invention may include preparing a connective tissue homogenate/carrier. Prior to homogenization, connective tissues (i.e., fascia, tendons, ligaments, pericardium, and cartilage, among others) may be crudely fragmented. Connective tissue (e.g., fresh or freeze-dried) may be sliced, ground, carved, chipped, chopped, minced, cut, dissected, rent, ripped, sectioned, snipped, diced, shaved, comminuted, or trimmed into crude fragments. In some embodiments, the crude fragments may have an average diameter greater than about 50 microns. The crude fragments may be of varying sizes, in some embodiments. Essentially intact connective tissue or crude fragments of connective tissue (e.g., fresh or freeze-dried) may be homogenized at least one time to prepare the homogenate. The homogenization step(s) of certain inventive methods may involve shear-induced shredding of connective tissue. Connective tissue may be homogenized to have tissue fragments having an average diameter of less than about 50 microns, less than about 20 microns, or less than about 50 microns and more than about 5 microns. Water, at least one aqueous solution (e.g., isotonic saline), a water-replacement agent, or other components may be combined with a connective tissue before homogenization.

Certain methods include at least one of (a) heating a connective tissue before it is homogenized, (b) heating a connective tissue while it is being homogenized, and (c) heating a connective tissue homogenate. In some embodiments the heating is done to a temperature of between about ambient temperature and about 100° C., or between about 37° C. and about 100° C. The heating may be carried out for between about 4 minutes and about 30 minutes. The heating may be accomplished using sonication, microwave irradiation, or conventional heat transfer from a heating component, among other methods known in the art.

In certain methods, the tissue repair composition may be cast in a mold. In some embodiments, a method may further include freeze-drying a cast composition or cross-linking a cast composition utilizing chemical reagents known in the art.

Methods of the current invention may include sterilization of tissue repair compositions, components of tissue repair compositions, and/or sterilization of packaged tissue repair compositions/components. Sterilization may be performed using methods known in the art. The sterilization may involve the use of ionizing radiation, in some embodiments. Methods of the current invention may include irradiation of tissue repair compositions, components of tissue repair compositions, and/or irradiation of packaged tissue repair compositions/components. Irradiation may be performed using methods known in the art. The irradiation may involve the use of ionizing radiation, in some embodiments. In certain embodiments, the absorbed dose of ionizing radiation may be between about 8.0 kGy and about 50 kGy, between about 8.0 kGy and about 25 kGy, and between about 8.0 kGy and about 18 kGy. In some embodiments, the sterilizing and/or irradiation step includes placing the packaged composition on dry ice and irradiating the packaged composition. In certain embodiments, sterilization and/or irradiation may be performed at a temperature of between about −20° C. and −50° C. In some embodiments of the present invention, the composition or component of a tissue repair composition that is irradiated after it has been freeze dried.

Certain methods of the present invention involve (a) providing at least one connective tissue and at least one bone tissue from at least one cadaver, (b) freeze-drying the connective tissue, (c) crudely fragmenting the connective tissue, (d) adding at least one of water, an aqueous solution (i.e., isotonic saline), a water-replacement agent, or a water miscible polar organic solvent to the crude fragments to produce a mixture, which may optionally be heated, (e) homogenizing the mixture to produce a connective tissue homogenate, (f) fragmenting the bone tissue to produce fragments, (g) optionally demineralizing the bone fragments, (h) freeze-drying the bone fragments, (i) selecting bone fragments having sizes within a particular range, (j) combining the selected bone fragments of the particular range with the connective tissue homogenate. Certain methods may include at least one of (a) heating a connective tissue before it is homogenized, (b) heating a connective tissue while it is being homogenized, (c) heating a connective tissue homogenate, and (d) heating the tissue repair composition. In some embodiments, heating is sufficient to reach a temperature of about 100° C. A microwave oven may be used in the heating step, in certain embodiments. Connective tissue homogenate may be heated and homogenized a second time before being combined with the bone fragments in certain methods of the present invention. In some embodiments, the selecting of bone fragments having sizes with a given range may involve the use of mesh sieves. In some embodiments, the tissue repair composition may be packaged, and the packaged composition may optionally be sterilized.

Certain embodiments of the present invention are directed to methods for producing a tissue repair composition including: (a) producing a connective tissue homogenate from one or more connective tissues; (b) mixing the connective tissue homogenate with at least one of water, an aqueous solution, a water-replacement agent, a bodily fluid, or a water miscible polar organic solvent to produce a carrier; (c) mixing at least one or more bone fragments with the carrier to produce a tissue repair composition; and (d) freezing or freeze-drying the tissue repair composition.

Some embodiments of the present invention are directed to methods for producing a tissue repair composition including: (a) producing a connective tissue homogenate from one or more connective tissues; (b) mixing the connective tissue homogenate with at least one of water, an aqueous solution, a water-replacement agent, a bodily fluid, or a water miscible polar organic solvent to produce a carrier; (d) freezing or freeze-drying the carrier; and (e) mixing at least one or more of the bone fragments with the freeze-dried carrier to produce a tissue repair composition. In certain embodiments, the freeze-dried carrier may be mixed with the bone fragments and packaged. In some embodiments, the freeze-dried carrier may be packaged separately, or as a kit with the bone fragments, which may be mixed right before implantation or surgery.

The steps set forth above for preparing inventive tissue repair compositions may be combined and the sequence of steps may be changed. In some embodiments, water, an aqueous solution, a water-replacement agent, or a water miscible polar organic solvent may be added to a connective tissue as it is homogenized to prepare a homogenate of connective tissue.

In certain embodiments, inventive tissue repair compositions of the present application may be applied to a prosthetic device utilized in neurological or orthopedic applications, to facilitate osteoconduction, and/or osteoinduction of native bone around the implant in order to build a stronger and more compatible association between the implant and the native bone. Implantable bone prostheses may include a substrate formed of a biocompatible metal, ceramic, mineral component, or composite; and at least a partial coating of tissue repair composition.

Certain embodiments of the present invention are directed to coated prosthetic devices including, an implantable prosthetic device, and a coating directly adjacent to at least a portion of a surface of the implantable prosthetic device. The coating includes at least one tissue repair composition including (a) a plurality of bone fragments and (b) a homogenized connective tissue.

Some embodiments of the present invention are directed to a method of coating a prosthetic device including, providing an implantable prosthetic device, and applying at least one tissue repair composition to at least a portion of a surface of the implantable prosthetic device. The tissue repair composition is as described above.

Certain embodiments of the present invention are directed to methods of promoting tissue repair or regeneration including applying a tissue repair composition as described above to a damaged tissue to promote repair or regeneration of the tissue. The tissue may be an osseous tissue, a cartilage, or a soft tissue. Soft tissues may include but are not limited to tendons, ligaments, muscles, synovium, blood vessels, and nerves. Some embodiments of the present invention are directed to methods of inducing bone or cartilage formation including applying a tissue repair composition as described above to an implant site to induce bone or cartilage formation.

The present invention also provides methods of using the tissue repair composition to heal or repair wounds or tissue defects.

The bioactive factor included in the compositions of the present invention may be an osteoinductive factor, a chondrogenic factor, a cytokine, a mitogenic factor, a chemotactic factor, a transforming growth factor (TGF), a fibroblast growth factor (FGF), an angiogenic factor, an insulin-like growth factor (IGF), a platelet-derived growth factor (PDGF), an epidermal growth factor (EGF), a vascular endothelial growth factor (VEGF), a nerve growth factor (NGF), a neurotrophin, a bone morphogenetic protein (BMP), osteogenin, osteopontin, osteocalcin, cementum attachment protein, erythropoietin, thrombopoietin, tumor necrosis factor (TNF), an interferon, a colony stimulating factor (CSF), or an interleukin, among others. The bioactive factor may be a BMP, PDGF, FGF, VEGF, TGF, insulin, among others. Examples of BMPs include but are not limited to BMP-2, BMP-3, BMP-4, BMP-5, BMP-6, BMP-7, BMP-8, BMP-9, BMP-10, BMP-11, BMP-12, BMP-13, BMP-14, and BMP-15. The bioactive factors included in the tissue repair compositions of the present invention may be a combination of one or more bioactive factors.

In one embodiment, the bioactive factor may be a growth factor selected from the group consisting of transforming growth factor beta, a fibroblast growth factor, a vascular endothelial growth factor, or a platelet derived growth factor. In another embodiment, the bioactive factor is a bone morphogenic protein or insulin.

The composition of the present invention may comprise bone fragments at between about 5 wt % and about 90 wt %, about 20 wt % and about 80 wt %, or about 30 wt % and about 50 wt %. The bone fragments may have an average diameter of between about 125 microns and about 4 mm, about 125 microns and 850 microns, about 125 microns and about 710 microns, about 125 microns and about 500 microns, about 250 microns and about 710 microns.

The demineralized bone fragments may have less than about 8 wt % residual calcium, less than about 4 wt % residual calcium, from about 0.5 wt % to about 4 wt % residual calcium, or from about 1 wt % to about 4 wt % residual calcium. The demineralized bone fragments may have between about 0 wt % to about 8 wt %, about 0.5 wt % and about 6 wt %, about 0.5 wt % and about 4 wt %, or about 2 wt % and about 4 wt % residual calcium.

The compositions of the present invention may include homogenized connective tissue in the amount of between about 0.25 wt % and about 80 wt %, about 0.5 wt % and about 5 wt %, or about 0.5 wt % and about 4 wt %. The homogenized connective tissue may be homogenized fascia, homogenized tendon, homogenized ligament, homogenized pericardium, homogenized cartilage, or a mixture thereof. The homogenized connective tissue may be acellular.

In one embodiment, the composition of the present invention may comprise bone fragments from a single donor source or multiple donor sources. In another embodiment, the composition of the present invention may comprise homogenized connective tissue from a single donor source or multiple donor sources. The composition of the present invention may also comprise an osteoconductive component.

The compositions of the present invention may also include a calcium phosphate mineral and a calcium sulfate mineral. The mineral may harden prior to or post implantation.

The composition of the present invention may also include hydroxyapatite particulates, calcium phosphate particulates, magnesium phosphate particulates, and calcium carbonate particulates.

The compositions of the present invention may further include cortical bone fragments, cancellous bone fragments and ground/milled cortical bone fragments.

The present invention provides a coated, prosthetic device comprising an implantable prosthetic device, wherein at least a portion of a surface of the implantable prosthetic device is coated with a composition of the present invention, such as a tissue repair composition. The tissue repair composition may comprise a plurality of bone fragments, or a combination thereof, and a carrier composition containing a carrier and one or more carrier compounds; and wherein the carrier consists of or consists essentially of one or more homogenized connective tissues.

The present invention also provides a method of coating a prosthetic device comprising applying a composition of the present invention, such as a tissue repair composition, to at least a portion of a surface of the implantable prosthetic device, wherein the tissue repair composition comprises a plurality of bone fragments, and a carrier composition containing a carrier and one or more carrier compounds; and wherein the carrier consists essentially of one or more homogenized connective tissues.

Moreover, the present invention provides implanting a coated, prosthetic device at an osseous implant site wherein the method includes preparing an osseous implant site, and implanting the coated, prosthetic device of the present invention at the implant site.

In one embodiment, the method of coating the prosthetic device further comprises freeze-drying the tissue repair composition on the surface of the implantable prosthetic device. Accordingly, the present invention may also include a coated prosthetic device, wherein the tissue repair composition is freeze-dried onto the surface of the implantable prosthetic device. In another embodiment, the method further comprises freeze-drying the tissue repair composition prior to applying it to the surface of the prosthetic device.

The method may comprise applying a chemical reagent to the surface of the prosthetic device. The method may also include shaping the tissue repair composition using a mold after applying the tissue repair composition to the surface of the prosthetic device. Moreover, the method may include freeze-drying the tissue repair composition after shaping the tissue repair composition.

Without further description, it is believed that one of ordinary skill in the art can, using the preceding description and the following illustrative examples, make and utilize the claimed invention. The following working examples therefore, specifically point out embodiments of the present invention, and are not to be construed as limiting in any way the remainder of the disclosure. All articles, publications, patents and documents referred to throughout this application are hereby incorporated by reference in their entirety.

Further details of the process of the invention are presented in the examples that follow:

EXAMPLES

Example 1

Preparation of Tissue Repair Compositions Containing Freeze-Dried Fascia

Fascia lata and bone from a human cadaver were procured and returned to the processing facility under sterile conditions. Donor histories, personal and medical, were obtained following accepted standards of the American Association of Tissue Banks Microbiological tests were performed following FDA guidelines for testing sterility of products.

The bone and fascia were cleaned of unwanted tissues and freeze-dried. The freeze-dried fascia was cut into small (about ½ cm by ½ cm) pieces (e.g., crude fragments). Isotonic saline in a volume (1 cm$^3$ of isotonic saline corresponds to about 1 g) approximating 20 times the weight of tissue, was added to a container containing the cut fascia. The ingredients were heated to a temperature of 100° C. using a microwave oven, and maintained at this temperature for 4 minutes. Water was added to the heated composition to replace the liquid lost to evaporation. The heated composition was transferred into a conventional blender and mechanically homogenized (e.g., blended) for 5 minutes. The homogenized connective tissue was re-heated for an additional 4 minutes in the microwave oven, and mechanical homogenization was repeated for an additional 5 minutes (e.g., until the mixture was liquefied and homogeneous).

Ground demineralized bone powder was prepared by impact fragmentation of bone, followed by freeze-drying. The freeze-dried particles were sized using mesh sieves. Ground demineralized bone particles having a size in the range of about 250 to 710 microns and demineralized to an average weight percent residual calcium of 2±1% were used.

To prepare a first tissue repair composition, the sized, freeze-dried demineralized bone powder was added to the homogenized fascia until the final concentration of the bone was about 30% by weight. In a second tissue repair composition, the demineralized bone powder was added to the homogenized fascia until the final concentration of the bone was about 65% by weight. Samples of the tissue repair composition were sealed in sterilized glass vials in 2 g aliquots.

Example 2

Preparation of a Tissue Repair Composition Containing Freeze-Dried Tendon

Tendon and bone from a human cadaver were procured and returned to the processing facility under sterile conditions. Donor histories, personal and medical, were obtained following accepted standards of the American Association of Tissue Banks Microbiological tests were performed following FDA guidelines for testing sterility of products.

The bone and tendons were cleaned of unwanted tissues and freeze-dried. The freeze-dried tendon was cut into small (about ½ cm by ½ cm) pieces (e.g., crude fragments). Isotonic saline in a volume (1 cm$^3$ of isotonic saline corresponds to about 1 g) approximating 20 times the weight of tissue, was added to a container containing the cut fascia. The ingredients were heated to a temperature of 100° C. using a microwave oven, and maintained at this temperature for 4 minutes. Water was added to the heated composition to replace the liquid lost to evaporation. The heated composition was transferred into a conventional blender and mechanically homogenized (e.g., blended) for 5 minutes. The homogenized connective tissue was re-heated for an additional 4 minutes in the microwave oven, and mechanical homogenization was repeated for an additional 5 minutes (e.g., until the mixture was liquefied and homogeneous).

Ground demineralized bone powder was prepared by impact fragmentation of bone, followed by freeze-drying. The freeze-dried particles were sized using mesh sieves. Ground demineralized bone particles having a size in the range of about 250 to 710 microns and demineralized to an average weight percent residual calcium of 2±1% were used.

In order to prepare the tissue repair composition, the freeze-dried demineralized bone powder was added to the heated, homogenized tendon tissue until the final concentration of the bone in the tissue repair composition was about 30% by weight. Samples were sealed in sterilized glass vials in 2 g aliquots.

Example 3

Preparation of Tissue Repair Compositions Containing Non-Freeze-Dried Fascia

Fascia and bone from a human cadaver were procured and returned to the processing facility under sterile conditions. Donor histories, personal and medical, were obtained following accepted standards of the American Association of Tissue Banks Microbiological tests were performed following FDA guidelines for testing sterility of products.

The bone and fascia were cleaned of unwanted tissues and the bone was freeze-dried. Fresh, non-freeze-dried fascia was used. The fascia was cut into long strips and was mixed with water at a ratio of about 1:15 by weight. The ingredients were heated to a temperature of 100° C. using a microwave oven, and maintained at this temperature for 4 minutes. Water was added to the heated composition to replace the liquid lost to evaporation. The heated composition was transferred into a conventional blender and mechanically homogenized (e.g., blended) for 5 minutes. The homogenized connective tissue was re-heated for an additional 4 minutes in the microwave oven, and mechanical homogenization was repeated for an additional 5 minutes (e.g., until the mixture was liquefied and homogeneous).

Ground demineralized bone powder was prepared by impact fragmentation of bone, followed by freeze-drying. The freeze-dried particles were sized using mesh sieves. Ground demineralized bone particles having a size in the range of about 250 to 710 microns and demineralized to an average weight percent residual calcium of 2±1% were used.

To prepare a first tissue repair composition, the demineralized bone powder was added to the homogenized, non-freeze-dried fascia until the final concentration of the bone was about 30% by weight. In a second tissue repair composition, the demineralized bone powder was added to a final concentration of about 65% by weight. Samples of the tissue repair compositions were sealed in sterilized glass vials in 2 g aliquots.

Example 4

Preparation of a Tissue Repair Composition Containing Rehydrated Freeze-Dried Fascia and Rehydrated Freeze-Dried Bone Fascia and bone from a human cadaver were procured and returned to the processing facility under sterile conditions. Donor histories, personal and medical, were obtained following accepted standards of the American Association of Tissue Banks Microbiological tests were performed following FDA guidelines for testing sterility of products.

The bone and fascia were cleaned of unwanted tissues and freeze-dried. The fascia was rehydrated prior to being used in making of the composition. The rehydrated fascia was cut into small (about ½ cm by ½ cm) pieces (e.g., crude fragments). Isotonic saline in a volume (1 cm$^3$ of isotonic saline corresponds to about 1 g) approximating 20 times the weight of tissue, was added to a container containing the cut fascia. The ingredients were heated to a temperature of 100° C. using a microwave oven, and maintained at this temperature for 4 minutes. Water was added to the heated composition to replace the liquid lost to evaporation. The heated composition was transferred into a conventional blender and mechanically homogenized (e.g., blended) for 5 minutes. The homogenized connective tissue was re-heated for an additional 4 minutes in the microwave oven, and mechanical homogenization was repeated for an additional 5 minutes (e.g., until the mixture was liquefied and homogeneous).

The ground demineralized bone powder was prepared by impact fragmentation, followed by freeze-drying, and finally the particles were sized using mesh sieves. Ground demineralized bone particles having a size in the range of about 125 to 500 microns were used.

The freeze-dried demineralized bone particles were rehydrated prior to being combined with the homogenized fascia. The final concentration of the bone particles in the tissue repair composition was about 20 wt % after rehydration. The resulting tissue repair composition was a gel. The gel was packaged in 5 ml Luerlock syringes. The gel was easily extruded from the syringe. A thirteen-gauge needle was attached to the syringe, and the gel was easily extruded through the needle, as well.

Example 5

Preparation of a Molded Tissue Repair Composition Containing Freeze-Dried Fascia Fascia and bone from a human cadaver were procured and returned to the processing facility under sterile conditions. Donor histories, personal and medical, were obtained following accepted standards of the American Association of Tissue Banks Microbiological tests were performed following FDA guidelines for testing sterility of products.

The bone and fascia were cleaned of unwanted tissues and freeze-dried. The freeze-dried fascia was cut into small (about ½ cm by ½ cm) pieces (e.g., crude fragments). Isotonic saline in a volume (1 $cm^3$ of isotonic saline corresponds to about 1 g) approximating 20 times the weight of tissue, was added to a container containing the cut fascia. The ingredients were heated to a temperature of 100° C. using a microwave oven, and maintained at this temperature for 4 minutes. Water was added to the heated composition to replace the liquid lost to evaporation. The heated composition was transferred into a conventional blender and mechanically homogenized (e.g., blended) for 5 minutes. The homogenized connective tissue was re-heated for an additional 4 minutes in the microwave oven, and mechanical homogenization was repeated for an additional 5 minutes (e.g., until the mixture was liquefied and homogeneous).

Ground demineralized bone powder was prepared by impact fragmentation of bone, followed by freeze-drying. The freeze-dried particles were sized using mesh sieves. Ground demineralized bone particles having a size in the range of about 125 to 710 microns and demineralized to an average weight percent residual calcium of 2±1% were used.

In order to prepare the tissue repair composition, the freeze-dried demineralized bone powder was added to the homogenized fascia until the final concentration of the bone in the composition was about 40% by weight. The tissue repair composition was then placed into different containers and molds, and freeze-dried using a two-day cycle as prescribed by the manufacturer of the freeze-drier. The freeze-dried, molded, tissue repair compositions demonstrated high mechanical strength and maintained the shape of their mold. The cast tissue repair composition may be rehydrated using an isotonic solution to make it malleable or may be cross-linked with a fixative such as glutaraldehyde, EDC (1-ethyl-3-(3-dimethylaminopropyl) carbodiimide), or genapin to help retain its solid, rigid, molded form to be used in applications where a specific shape and mechanical strength would be desirable.

Example 6

Preparation of Tissue Repair Compositions Containing Freeze-Dried Fascia

Fascia and bone from a human cadaver were procured and returned to the processing facility under sterile conditions. Donor histories, personal and medical, were obtained following accepted standards of the American Association of Tissue Banks Microbiological tests were performed following FDA guidelines for testing sterility of products. The bone and fascia were cleaned of unwanted tissues and freeze-dried.

Ground demineralized bone powder was prepared by impact fragmentation of bone, followed by freeze-drying. The freeze-dried particles were sized using mesh sieves. Ground demineralized bone particles having a size in the range of about 125 to 500 microns and demineralized to an average weight percent residual calcium of 2±1% were used.

The small pieces of connective tissue and the saline solution were brought to a temperature of 100° C. using a heating plate and the mixture was heated at this temperature for an additional 5 minutes. Water was added to the mixture to replace the solution lost due to evaporation. The mixture was transferred into a conventional blender and mechanically homogenized at approximately 15,000 rpm (maximum shear speed of the commercially available blender) for 5 minutes. The mixture was again heated to a temperature of 100° C. using the heating plate, and maintained at this temperature for an additional 5 minutes. The heated mixture was again blended for two, 2-minute pulses to produce the homogenized fascia.

To prepare a first tissue repair composition, the sized, freeze-dried demineralized bone powder was added to the homogenized fascia until the final concentration of the bone was about 30% by weight. In a second tissue repair composition, the demineralized bone powder was added to the homogenized fascia until the final concentration of the bone was about 50% by weight.

Example 7

Preparation of Tissue Repair Compositions Containing Freeze-Dried Fascia

Fascia and bone from a human cadaver were procured and returned to the processing facility under sterile conditions. Donor histories, personal and medical, were obtained following accepted standards of the American Association of Tissue Banks Microbiological tests were performed following FDA guidelines for testing sterility of products.

The bone and fascia were cleaned of unwanted tissues and freeze-dried. The freeze-dried fascia was cut into small, ½ cm by ½ cm pieces (e.g., crude fragments). Isotonic saline in a volume (1 $cm^3$ of isotonic saline corresponds to about 1 g) approximating 50 times the weight of the tissue to be processed was added to cut fascia. The fascia and saline were brought to a temperature of 100° C. using a heating plate and was heated at this temperature for an additional 5 minutes. Water was added to replace the solution lost due to evaporation. The heated material was transferred into a blender and mechanically modified at 15,000 rpm (maximum shear speed of the commercially available blender) for 5 minutes. The homogenized connective tissue was again heated to a temperature of 100° C. using the heating plate, and maintained at this temperature for an additional 5 minutes. The heated homogenate was blended for two, 2-minute pulses. The material was divided and placed into centrifuge containers and spun at 1000 rcf for 5, 7, 9, and 10 minutes, respectively. Water in the material separated into a distinct layer after the centrifugation process. The volume of the water-layer was proportional to the centrifugation time. The materials remaining after removal of the water layer had different consistencies. To prepare tissue repair compositions, the sized, freeze-dried demineralized bone powder was added to the various homogenized materials until the final concentration of the bone was about 30% by weight. The viscosities of the tissue repair compositions correlated to the differing consistencies of the homogenized connective tissue materials used in their preparation.

Example 8

Determination of New Bone Formation

Fascia lata and bone from a human cadaver were procured and returned to the processing facility under sterile conditions. Donor histories, personal and medical, were obtained following accepted standards of the American Association of Tissue Banks Microbiological tests were performed following FDA guidelines for testing sterility of products.

The bone and fascia were cleaned of unwanted tissues and freeze-dried. The freeze-dried fascia was cut into small (about ½ cm by ½ cm) pieces (e.g., crude fragments). Isotonic saline in a volume (1 $cm^3$ of isotonic saline corresponds to about 1 g) approximating 20 times the weight of tissue, was added to a container containing the cut fascia. The ingredients were heated to a temperature of 100° C. using a microwave oven, and maintained at this temperature for 4 minutes. Water was added to the heated composition to replace the liquid lost to evaporation. The heated composition was transferred into a conventional blender and mechanically homogenized (e.g., blended) for 5 minutes. The homogenized connective tissue was re-heated for an additional 4 minutes in the microwave oven, and mechanical homogenization was repeated for an additional 5 minutes (e.g., until the mixture was liquefied and homogeneous).

Ground demineralized bone powder was prepared by impact fragmentation of bone, followed by freeze-drying. The freeze-dried particles were sized using mesh sieves. Ground demineralized bone particles having a size in the range of about 250 to 710 microns and demineralized to an average weight percent residual calcium of 2±1% were used.

Tissue repair compositions having a putty-like consistency were prepared by adding the sized, freeze-dried demineralized bone powder to the homogenized fascia until the final concentration of the bone was about 24%, 26%, 30%, and 50% by weight, respectively.

The prepared tissue repair compositions, a demineralized bone matrix (DBM) control (without homogenized connective tissue), and a homogenized tissue sample without DBM were implanted heterotopically (e.g., into muscle pouches) in the hind quarters of athymic (e.g., nude) mice. Each implant (other than the homogenized tissue-only sample) contained 20 mg of demineralized bone matrix. The amounts of materials implanted were varied to always implant 20 mg of DBM i.e., 40 mg of the 50% DBM composition was implanted. In that the DBM constituted 50% by weight, and the homogenized connective tissue constituted 50% by weight, the total implant of 40 mg contained 20 mg of DBM. Thus, 85 mg, 77 mg, 68 mg, and 40 mg of the 24 wt %, 26 wt %, 30 wt %, and 50 wt % tissue repair compositions were implanted, respectively. Three mice with two implants per mouse were used for each of the four tissue repair compositions, the DBM control, and the homogenized tissue-only sample (e.g., 18 mice in all and 36 implants).

After 28 days, the implants were explanted, and one explant from each mouse was fixed. At least one histological section was cut from the center of each of these explants. Samples were fixed in 10% buffered formalin. Standard dehydration, embedding and sectioning protocols were used to produce light microscopy slides that were subsequently stained with hematoxylin and eosin. Using histomorphometric analysis, the percent new bone formed was calculated as a cross-sectional area of newly formed bone ($mm^2$) divided by the total cross-sectional area ($mm^2$) for a representative microscopic view of a histology slide multiplied by 100. Every other field of view with at least 50% bone content was used as a representative view with about 10 representative views being analyzed per slide.

The demineralized bone that was implanted without homogenized connective tissue (e.g., the control) produced about 9.6% new bone growth, and the homogenized fascia alone (freeze dried material) produced about 3.8% new bone growths. The 24%, 26%, 30%, 50% demineralized bone to homogenized connective tissue compositions resulted in about 6.4%, 11.1%, 14.5%, and 16.2% new bone growth, respectively.

Example 9

Use of Radioprotectants

To meet the current U.S. FDA regulatory standards and market expectations, a product must be sterile to a sterility assurance level of $1 \times 10^{-6}$ (SAL). It was found that tissue repair compositions comprising HCT and bone fragments after gamma irradiation do not maintain their malleablity and tenaciousity after irradiation. The composition crumbled apart releasing the bone matrix.

In order to manufacture a tissue repair composition, in the form of a putty/paste, having desirable handling characteristics post-irradiation at dose designed to achieve a SAL of $1 \times 10^{-6}$, it was thought that the addition of one or more radioprotectants to the composition would produce a product with the desirable handling properties because the radioprotectant will act as a free radical scavenger during the irradiation sterilization process and would protect the handling characteristics of the putty/paste composition. An addition facet was that the radioprotectant must not negatively interfere with the biological activity over time (shelf life).

Multiple radioprotectants (Table 1) were investigated over a range of concentrations and the handling characteristics of the resultant products were semi-quantitatively analyzed post-gamma irradiation. Those products that passed the semi-quantitative analysis went on to be implanted into athymic nude mice as a bioassay to assess osteoinductivity. For example, 100 mM aminoguanidine was found to have no negative impact on osteoinductivity and the handling characteristics after receiving a sterilizing dose of gamma irradiation.

The method to add the radioprotectant was consistent for each radioprotectant investigated. The slurry was made as described in example 1 (heating and blending cycles) and once completed, the radioprotectant of choice was added to the slurry in the form it was supplied from the manufacturer (powder or liquid).

TABLE 1

| Radioprotectants and Concentration Investigated | |
| --- | --- |
| Radioprotectant | Passed Osteoinductivity |
| Aminoguanidine (CAS 1937-19-5) | Yes |
| L-Ascorbic Acid, salt (CAS 14306-25-3) | Yes |
| L-Ascorbic Acid 2-phosphate sesquimagnesium salt (CAS 113170-55-1) | Yes |

Example 10

Preparation of Tissue Repair Composition Containing Non-Demineralized Bone and Fascia Fascia lata and bone from a human cadaver were procured and returned to the processing facility under sterile conditions. Donor histories, personal and medical, were obtained following accepted standards of the American Association of Tissue Banks Microbiological tests were performed following FDA guidelines for testing sterility of products.

The bone and fascia were cleaned of unwanted tissues and freeze-dried. The freeze-dried fascia was cut into small (about 1.5 cm by 1.5 cm) pieces (e.g., crude fragments). Sterile water in a volume (1 $cm^3$ of isotonic saline corresponds to about 1 g) approximating 20 times the weight of tissue, was added to a container containing the cut fascia. The ingredients were heated to a temperature of 100 degree C. using a hot plate, and maintained at this temperature for about 5 minutes. Optionally, water was added to the heated composition to replace the liquid lost to evaporation. The heated composition was transferred into a conventional blender and mechanically homogenized (e.g., blended) for about 1 to 3 minutes. The homogenized connective tissue was re-heated for an additional 3 minutes on a hot plate, and mechanical homogenization was repeated for an additional 4 minutes (e.g., until the mixture was liquefied and homogeneous).

Ground cortical (GC) bone powder was prepared by impact fragmentation of bone, followed by freeze-drying. The freeze-dried particles were sized using mesh sieves. Ground cortical bone particles having a size in the range of about 250 to 1000 microns were used.

To prepare the tissue repair implant, the homogenized fascia was mixed with the sized, freeze-dried ground cortical bone powder and glycerol, and freeze dried. The bone was about 15%, 30%, 50%, 60%, 85%, 95% by weight in the tissue repair composition. The tissue repair composition can be aliquoted to different volumes and optionally freeze-dried.

It is to be understood that while the invention has been described in conjunction with the detailed description thereof, the foregoing description is intended to illustrate and not limit the scope of the invention. Other aspects, advantages, and modifications are within the scope of the following claims.

The invention claimed is:

1. A method of making a carrier composition comprising mixing a connective tissue homogenate with one or more carrier compounds to produce a carrier composition, wherein the connective tissue homogenate consists essentially of one or more homogenized connective tissues.

2. The method of claim 1, wherein the carrier compound is selected from the group consisting of radioprotectants, water miscible polar organic compounds, water, natural polymers, synthetic polymers, antibiotics, antiviral agents, and polysaccharides.

3. The method of claim 2, wherein the radioprotectant is aminoguanidine and the water miscible polar organic compound is glycerol.

4. The method of claim 1, further comprising freeze-drying the connective tissue carrier.

5. A method of making a tissue repair composition comprising mixing the carrier composition made by the method according to claim 1 with a plurality of bone fragments to produce a tissue repair composition.

6. The method of claim 5, further comprising freeze-drying the tissue repair composition.

7. The method of claim 5, wherein the bone fragments are natural demineralized bone fragments, natural non-demineralized bone fragments, synthetic bone fragments, or a combination thereof.

8. The method of claim 7, wherein the carrier compound is selected from the group consisting of radioprotectants, water miscible polar organic compounds, water, natural polymers, synthetic polymers, antibiotics, antiviral agents, and polysaccharides.

9. The method of claim 8, wherein the radioprotectant is aminoguanidine and the water miscible polar organic compound is glycerol.

10. A method of promoting tissue repair or regeneration comprising applying the tissue repair composition made by the method according to claim 8 to a damaged tissue to promote repair or regeneration of the tissue.

11. A method of inducing bone or cartilage formation comprising applying the tissue repair composition made by the method according to claim 8 to an implant site to induce bone or cartilage formation.

12. The method of claim 5, wherein the method further comprises mixing the tissue repair composition with a bioactive factor.

13. A method of promoting tissue repair or regeneration comprising applying the tissue repair composition made by the method according to claim 5 to a damaged tissue to promote repair or regeneration of the tissue.

14. A method of inducing bone or cartilage formation comprising applying the tissue repair composition made by the method according to claim 5 to an implant site to induce bone or cartilage formation.

15. A method of promoting tissue repair or regeneration comprising applying the carrier composition made by the method according to claim 1 to a damaged tissue to promote repair or regeneration of the tissue.

16. A method of inducing bone or cartilage formation comprising applying the carrier composition made by the method according to claim 1 to an implant site to induce bone or cartilage formation.

* * * * *